United States Patent [19]

Grier et al.

[11] 4,035,174

[45] July 12, 1977

[54] NOVEL DIBICYCLO [3.1.1] AND [2.2.1] HEPTYL AND DIBICYCLO [3.1.1] AND [2.2.1] HEPTENYL POLYAMINES AND METHODS FOR THEIR PREPARATION

[75] Inventors: Nathaniel Grier, Englewood, N.J.; Richard A. Dybas, Center Square, Pa.; Robert A. Strelitz, Edison, N.J.

[73] Assignee: Merck & Co., Inc., Rahway, N.J.

[21] Appl. No.: 670,588

[22] Filed: Mar. 26, 1976

Related U.S. Application Data

[63] Continuation-in-part of Ser. No. 620,721, Oct. 9, 1975, abandoned, which is a continuation-in-part of Ser. No. 540,620, Jan. 13, 1975, abandoned.

[51] Int. Cl.$^2$ .................. A01N 9/20; C07C 87/16; C07C 87/02; C02C 5/02
[52] U.S. Cl. ........................... 71/67; 71/121; 260/563 P; 210/64; 424/325
[58] Field of Search ............ 260/563 C, 563 P; 71/67, 121; 424/325

[56] References Cited

U.S. PATENT DOCUMENTS

| 2,843,587 | 7/1958 | de Benneville ............ 260/563 P X |
| 3,483,254 | 12/1969 | Shen et al. ..................... 260/563 P |
| 3,629,333 | 12/1971 | Boughton et al. .............. 260/563 P |

FOREIGN PATENT DOCUMENTS

| 1,481,067 | 4/1967 | France ............................. 260/563 C |
| 844,827 | 8/1960 | United Kingdom ........... 260/563 C |
| 860,860 | 2/1961 | United Kingdom ........... 260/563 P |

*Primary Examiner*—Allen B. Curtis
*Attorney, Agent, or Firm*—Edmunde D. Riedl; Julian S. Levitt

[57] ABSTRACT

Novel dibicyclo [3.1.1] and [2.2.1] heptyl and dibicyclo [3.1.1] and [2.2.1] heptenyl polyamines having a cyclohexylene group in the polyamine moiety are useful antimicrobial agents, as well as algae inhibitors. They are especially useful as hard surface disinfectants and as additives to oil well drilling muds, injection brines and industrial waters where microbial control is desired.

22 Claims, No Drawings

NOVEL DIBICYCLO [3.1.1] AND [2.2.1] HEPTYL AND DIBICYCLO [3.1.1] AND [2.2.1] HEPTENYL POLYAMINES AND METHODS FOR THEIR PREPARATION

CROSS REFERENCE TO RELATED APPLICATONS

This application is a continuation-in-part of application, Ser. No. 620,721 filed Oct. 9, 1975 which in turn is a continuation-in-part of application, Ser. No. 540,620 filed Jan. 31, 1975, both now abandoned.

DISCLOSURE OF THE INVENTION

This invention relates to a new class of substituted polyamines which are useful as algae inhibitors and as broad spectrum antimicrobial agents, especially against gram-negative and anaerobic bacteria. The novel compounds of this invention have the structural formula:

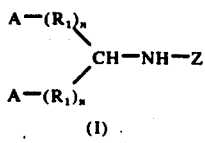

(I)

wherein:

Each A is alike or different and is substituted or unsubstituted [3.1.1] or [2.2.1] bicycloheptyl or bicycloheptenyl;

Each $n$ is alike or different and is the integer 0 1;
Each $R_1$ is alike or different and is $C_1$ to $C_4$ alkylene;
z is

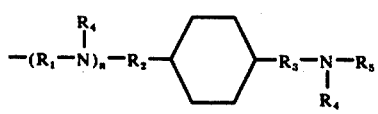

where
$R_2$ is 2-hydroxy-1,3-trimethylene, or $R_1$ as previously defined;
$R_3$ is 2-hydroxy-1,3-trimethylene, or $R_1$ as previously defined;
$R_4$ is hydrogen, aminoethyl, aminopropyl, $C_1$ to $C_4$ hydroxyalkyl, aminohydroxy $C_2$ to $C_4$ alkyl, or $C_2$ or $C_4$ dihydroxyalkyl;
$R_5$ is hydrogen, $C_1$ to $C_4$ hydroxyalkyl or $C_2$ to $C_4$ dihydroxyalkyl, aminohydroxy $C_2$ to $C_4$ alkyl, and $n$ is as previously defined.

When A is [2.2.1] bicycloheptyl or bicycloheptenyl, it has the formula:

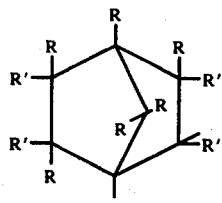

II where each R is alike or different and is $C_1$ to $C_4$ alkyl or hydrogen, R' is alike or different and is hydrogen or $C_1$ to $C_4$ alkyl or R' on adjacent carbon atoms can comprise an olefinic bond.

Generally, it is preferred that the sum of the number of carbon atoms in all the R and R' groups is ten or less.

In most preferred embodiments R' and R are independently hydrogen or methyl and less than five of all of R' and R are methyl. In the most highly preferred embodiments each A is either 3,3-dimethylnorborn-2-yl or norborn-2-yl and $R_1$ is ethylene or methylene.

When A is [3.1.1] bicycloheptyl or bicyclicheptenyl, it has the structural formula:

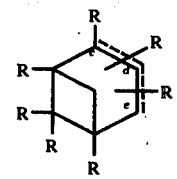

III where R is alike or different and is hydrogen or $C_1$ to $C_4$ alkyl and the dashed line indicates saturation or olefinic unsaturation either between the c- or d- or between the d- and e-positions, the bicyclo group being bonded to $(R_1)_n$ through the c-, d- or e-position of the ring. Preferred [3.1.1] bicyclic groups include those where R is methyl or hydrogen and no more than four R groups are methyl, such for example, as 2-, 3-, and 4-norpinanyl; 2-, 3-, and 4-(2-norpinenyl); 2-, 3-, and 4-(6,6-dimethylnorpinanyl); 2- and 4-(3,6,6-trimethyl-2-norpinenyl); 3-(2,4,6,6-tetramethyl-2-norpinenyl); 3- and 4-pinanyl; 3- and 4-(2-pinenyl); and 3- and 4-(3-pinenyl).

The compounds of this invention are generally prepared according to the following sequence of reactions:

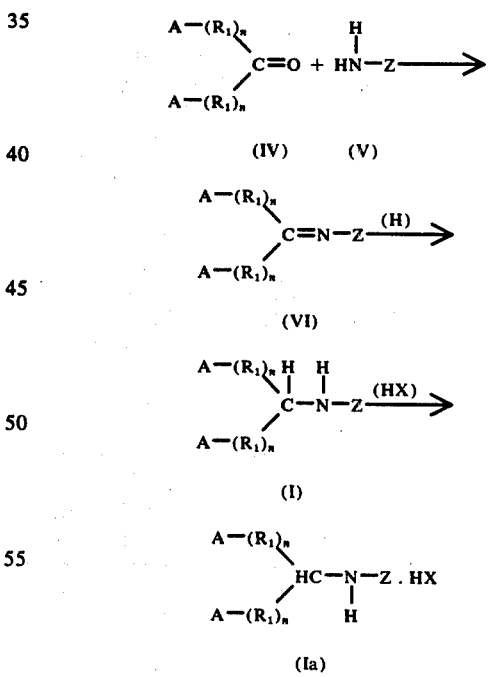

where A, Z and $n$ have their previously defined meanings, HX is a mono or polybasic organic or inorganic acid, where sufficient HX is provided to protonate at least one amino group of polyamine.

The preparation of polyamine I comprises the straightforward Schiff base reaction of the appropriate ketone IV and the appropriate amine V followed by reduction of the Schiff base VI to form polyamine I.

If amine V has two primary amino groups, it can either be symmetrical or unsymmetrical. An amine V, which is a symmetrical amine, e.g., where $R_2$ and $R_3$ are alike, $n$ is 1, and $R_4$ and $R_5$ are hydrogen, forms a single Schiff base VI. This is because regardless of which terminal primary amine group of amine V reacts with ketone IV, the same product results. However, where amine V is unsymmetrical at least two products can result. For example, if $R_4$ is either aminoethyl or aminopropyl, there is obtained Schiff base VI

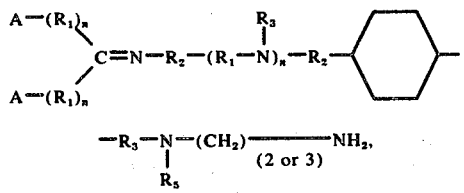

as well as Schiff base VI(a)

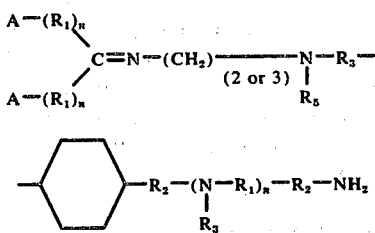

where A, $R_{1-6}$ and $n$ are as previously defined. Note that both products VI and VI(a) come within the scope of the definition given for Schiff base VI. Where multiple products such as from Schiff bases of formulas VI and VI(a) are produced, they can be separated, if desired, by the usual and well known separation techniques, i.e., distillation and the like.

As an alternative to obtaining a mixture of Schiff bases VI and VI(a) or VI(b), which upon reduction give a mixture of product I the reaction can be conducted stepwise. For example, 1,4-bis-(2-aminoethyl)-cyclohexane may be converted to a Schiff base with 1,5-di-[3,3-dimethylbicyclo[2.2.2]-hept-2-yl]pentan-3-one catalytically reduced, then the resulting amine selectively cyanoethylated with acrylonitrile, followed by catalytic hydrogenation to furnish N-(3-aminopropyl)-N'-[1,5-di-(3,3-dimethylbicyclo[2.2.1]-hept-2-yl)-3-pentyl]-1,4-bis-(2-aminoethyl)cyclohexane.

To prepare Schiff base VI, ketone IV and amine V are dissolved in a suitable inert solvent, for example, toluene, and heated to reflux, until reaction is substantially complete. Usually 5 to 20 hours is sufficient for water removal by azeotropic distillation. The solvent is then removed under reduced presure and the residue comprising the Schiff base VI is dissolved in an inert solvent preferably an alkanol, such as ethanol or isopropanol.

After dissolution, the Schiff base VI is catalytically or chemically reduced.

If reduction is catalytic, any unsaturated carbon to carbon bonds in A will also be reduced or hydrogenated, as well as the carbon to nitrogen bond to the Schiff base VI. In such catalytic reductions, hydrogen saturates an alkanol solution of Schiff base VI using agitation in the presence of the usual hydrogenation catalysts, such as transition metals and their reducible oxides. Especially effective catalysts are the noble metals and their oxides. A particularly preferred catalyst is platinum oxide. Generally, the hydrogenation reaction is carried out in a manner well known in the art. Small particles, e.g., 100–300 mesh of ctalyst are admixed with the Schiff base and excess amine in alcohol and placed in a closed system pressurized with from 3–5 atmospheres of hydrogen gas. After reaction is complete, the pressure is released and the catalyst separated from the reaction mixture by filtration. The filtrate containing the bicycloheptyl polyamine I, in then further purified by usual techniques. Preferably, whatever solvent may be present is removed under reduced pressure, the residue then dissolved in diethylether, washed with water, followed by a further washing with a saturated aqueous sodium chloride solution. After drying over anhydrous sodium sulfate, the diethylether is removed by evaporation under reduced pressure giving the bicycloheptylpolyamine I usually as an oil. The bicycloheptylpolyamine may then be redissolved in loweralkanols, mixtures of loweralkanols and water, diethylether or dioxane and then neutralized with an acid, e.g., hydrogen chloride, or neutralized directly with aqueous acids.

Acid addition satls are then isolated, if desired by precipitation, evaporation or other usually employed techniques.

Suitable anions X for the salt I(a) include anions derived from inorganic acids as well as those of organic acids such for example as halide, e.g., chloride, bromide or iodide or sulfate, bisulfate, nitrate, phosphate, acetate, propionate, maleate, succinate, laurate, oleate, palmitate, stearate, ascorbate, gluconate, citrate, carbonate, bicarbonate, benzoate, salicylate, pamoate phthalate, furoate, picolinate, dodecylbenzenesulfonate, laurylethersulfate, nicotinate and the like. Generally, any anion derived from an acid is suitable and satisfactory when the polyamine salt anion $X^-$, e.g., chloride, is to be replaced with other anions by, for example, well known anion exchange techniques.

When preparing bicycloheptenylpolyamines, that is the product I where olefinic unsaturation in ring A is retained, a selective chemical rather than a catalytic reduction is employed to reduce Schiff base VI to product I.

In this chemically reductive procedure, the ketone IV is reacted with the appropriate amine as before, but the Schiff base VI dissolved in an inert alkanol or ether-type solvent is reacted with a chemical reductant such as sodium borohydride or lithium aluminum hydride, respectively. Although as little as an equivalent of the chemical reductant can be used successfully, more satisfactory results are obtained if at least two molar excess of and preferably at least a 2.5 molar excess of the chemical reductant is employed. After any initial reaction has subsided, the reaction mixture of Schiff base VI and reductant may be heated to reflux for an hour or two, then cooled to room temperature, and afterwards concentrated under vacuum. The residue obtained is then further purified as by treatment with mineral acid or inorganic base as was described for bicycloheptylpolyamines I and the salt may thereafter be formed as previously described.

The bicycloheptyl and bicycloheptenyl ketones IV are prepared by four alternative methods, which are set forth below as (A) through (D).

A. The Condensation of Acids

This method involves the following reaction scheme:

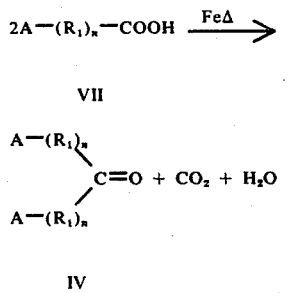

Acylative decarboxylation of acids VII is employed by heating the acid at elevated temperatures either with transition metals, preferably iron, transition metal oxides, alkaline earth oxides, with polyphosphoric acid or with boron trifluoride. Most suitably, acylative reaction is achieved by passage of acid vapors over catalysts such as heated thoria aerogel.

Condensation-decarboxylation of an acid is the preferred method for preparing ketone IV when each A-$(R_1)_n$ group is alike, a mixture of products being obtained when several different sides are combined in a reaction. The preferred reaction comprises admixing carboxylic acid VII with reduced iron powder and stirring in an inert atmosphere at 195° C. to 200° C. for 1–6 hours to form an iron salt.

Preferably, the carboxylic acid VII and iron are agitated under an inert atmosphere of nitrogen for at least 2 hours at 195° C. to 200° C.

After 2 hours, the temperature is increased suitably to 290° C. to 295° C. and agitation continued for at least another three hour period, four hours usually being sufficient. The reaction mixture is allowed to cool, the then is extracted with a suitable inert solvent such as diethylether and filtered. The solvent extracts are concentrated under reduced pressure. The residual liquid is distilled under vacuum to isolate the ketone IV.

The carboxylic acids VII employed above are prepared by various means well known in th art. One particularly useful technique is the addition of [2.2.1] bicycloheptenes, such for example, either camphene, isocamphodiene, β-fenchene, norbornylene, santene and the like to an aliphatic acid anhydride.

In this procedure, a mixture of the bicyclicheptene and a catalytic quantity, e.g., 0.2–0.3 mole for each mole of terpene of a free radical-forming catalyst, such as di-tert-butyl peroxide, is added dropwise over 3–5 hours to a 5–15 molar excess of refluxing aliphatic acid anhydride. After complete addition, the reaction is heated at reflux for 5–10 hours, concentrated under reduced pressure and the liquid residue is mixed with aqueous sodium hydroxide and stirred with heating on a steam bath for about 2–5 hours. The cooled alkaline solution is then extracted with ether, the ether layer is discarded and the aqueous solution acidified, and then extracted well with ether. The combined ether extracts are washed with water, dried over anhydrous sodium sulfate, and concentrated under reduced pressure. The residual liquid or solid is distilled under vacuum to give the corresponding carboxylic acid, VII.

Other carboxylic acids are readily obtained, for example, by the Diels-Adler reaction of cyclopentadiene and alkyl substituted cyclopentadiene with various unsaturated carboxylic acids, as are later referred to in greater detail.

Another useful general procedure for this synthesis of the bicyclo [2.2.1] heptyl substituted alkanoic acid compounds utilizes the free radical catalyzed addition of methyl or ethyl alkanoate to unsaturated bicyclo [2.2.1] heptenes. The free radical catalysis is obtained with, for example, di-t-butyl peroxide which predominantly abstracts a carbonyl-adjacent hydrogen from the alkyl alkanoate [D. J. Trecker and R. S. Foote, J. Org. Chem., 33, 3527–34 (1968)]. Addition of the resultant free radical to the olefinic terpene provides the corresponding esters. Usual hydrolysis procedures, e.g., with dilute aqueous sodium hydroxide result in alcohol liberation.

B. Condensation of a Grignard and a Nitrile

Disubstituted bcyclohepytl or bicycloheptenyl alkanones can also be obtained according to the following reaction scheme.

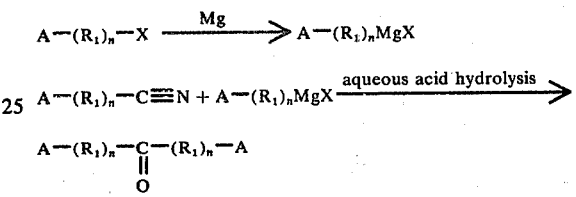

where $(R_1)_n$ of each reactant may be the same or different

In the preparation of di-(substituted bicycloheptyl)alkanones a general procedure utilize the reaction of a Grignard reagent prepared from a chloro- or bromo-substituted alkylbicyclo [2.2.1] heptane with a cyano-substituted alkyl bicyclo [2.2.1] heptane. The resultant disubstituted iminoalkane salt complex is hydrolyzed with mineral acid to the corresponding ketone.

The Grignard reagent is obtained by reaction of the halide with magnesium metal, usually in the form of turnings or powder and catalyzed by very small concentrations of iodine or methyl iodide. Solvents which are useful include diethyl ether, dibutyl ether, tetrahydrofuran, dioxane and benzene. Usually, gentle warming suffices to initiate the reaction and the halide is gradually added to the metal-solvent mixture. After complete addition the disappearance of practically all magnesium metal signifies the end of the reaction. A small excess of metal is used and moisture must be excluded; a nitrogen atmosphere is beneficial. The nitrile in two to three times its volume of solvent is then added to the Grignard reagent over a period of 15 minutes to 1 hour at ambient temperature. The reaction mixture may then be heated to reflux to insure complete reaction. Generally, a small excess of Grignard reagent as compared to nitrile is employed. From 1 to 10 hours at reflux is sufficient for complete conversion. The resultant imine salts is preferably decomposed to the ketone with aqueous mineral acids such as hydrochloric, sulfuric and phosphoric. The ketones are water-insoluble and may be extracted with water-immiscible solvents. Purification is preferably accomplished by fractional distillation under reduced pressure. It is feaasible to use the crude ketone reaction mixture for the alkylation of polyamines as the reaction by-products are usually alcohols or hydrocarbons and do not react with amines. The reactant halides, if present in the crude product, should be removed prior to the ketone-amine alkylation process.

The concentrations of Grignard reagent and nitrile may be varied over wide limits for securing good yields in the process.

The halide and cyano, as well as carboxylic derivatives of bicycloheptanes and bicycloheptenes, are commonly available and have been derived from such bicycloheptenes and norcamphane, apocamphane, camphane, α-fenchane, santane, camphenilane, αfenchane, isocamphane, α-fenchane, norbornylene, apobornylene, bornylene, δ-fenchene, camphenilene, γ-fenchene, santene, ε-fenchene, norpinane, 2-norpinane, 6,6-dimethylnorpinane, 6,6-dimethyl-2-norpinane, orthodene, homopinene, pinane, α-pinene, β-pinene, and the like.

Where these carboxylic, cyano, or halo derivatives are not readily available they may be synthesized by known techniques. For example, the Diels-Alder condensation as reported in U.S. Pat. No. 3,595,917 and *Newer Methods of Preparative Organic Chemistry*, K. Alder Interscience, New York, New York, 1948, pages 381–456, e.g.,

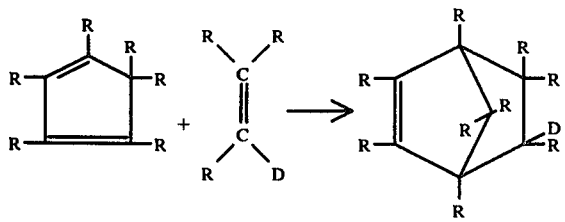

where D is R, $-(R_1)_n-COOH$, $-(R_{1n}-X$, or $-(R_1)_n-CN$ and where $R_1$, R, and X have their previous meanings. Where D is R and each R is alkyl, the resulting bicycloheptene can be reacted with an aliphatic acid anhydride as previously described.

c. The reaction of Acid Halides and Malonic Esters

The third alternative method for preparing ketones IV employs the reaction scheme:

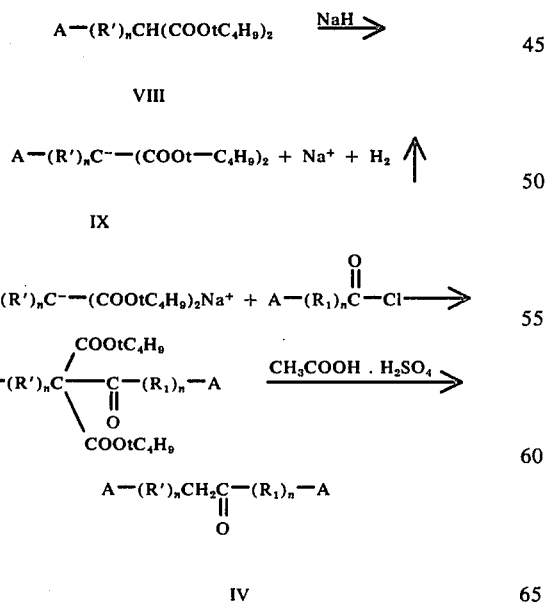

where A, $R_1$, and $n$ have their previous meanings and R' is $C_1$ to $C_3$ alkylene.

The bicyclo [2.2.1] heptylsubstituted malonic esters are prepared by way of example either from cyclopentadienes and alkenyl substituted malonic esters followed by catalytic hydrogenation of the resultant heptene derivatives to heptanes or by alkylation of malonic esster with a halogen-substituted bicyclo [2.2.1] heptane, the halogen preferably chlorine or bromine attached directly to the ring or as part of an alkyl substituent.

The sodio derivative IX of t-butyl malonic ester is prepared by adding a slight molar excess of sodium hydride to a solution of the malonic ester VIII in an inert solvent such anhydrous benzene. Reaction is effected by heating suitably to 60° C. to 80° C. with agitation until hydrogen gas evolution ceases, the reaction system being protected from atmospheric moisture. A solution of a equimolar quantity of acid halide X using sufficient anhydrous benzene to just dissolve the acid halide is added and the reaction heated at reflux for about 5–20 minutes. The mixture is cooled and any excess sodium hydride is destroyed by the addition of anhydrous p-toluene sulfonic acid. The reaction mixture is clarified by filtration and stripped of solvent under reduced pressure. The residue is dissolved in glacial acetic acid containing 0.3%–0.5% by weight anhydrous p-toluene sulfonic acid and approximately 2% by volume of acetic anhydride. The solution is heated to reflux for about an hour than cooled to room temperature. The solution is then poured over ice, neutralized with aqueous sodium hydroxide and the crude ketone IV product extracted with diethyl ether. The ether solution is washed with water, dried over anhydrous magnesium sulfate, filtered and stripped of solvent.

(D) Condensation of a Ketone with a Ketone or Aldehyde and Subsequent Reduction

A fourth method for preparing ketone IV employs the condensation of a ketone and a ketone or aldehyde according to the following reaction scheme:

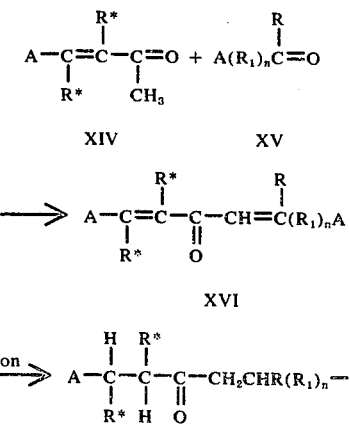

where A is alike or different and A, $R_1$, R and n have their previous definitions, and R* is independently methyl, ethyl or hydrogen.

The reaction comprises mixing the ketone XIV with a molar equivalent or slight excess of aldehyde or ketone XV with agitation and cooling in the presence of catalytic amounts of sodium methylate. The reaction mixture now is maintained at 40° C–55° C. for about 4–10 hours and then cooled at ambient temperature. The reaction mixture is acidified and after stripping the solvent under reduced pressure, the residue is extracted with diethyl ether. The ether extracts are washed with water and dried over magnesium sulfate. The solvent is then stripped under reduced pressure.

The residue XVI is dissolved in thiophene-free benzene and shaken under a pressure of 3–5 atmospheres of hydrogen in the presence of a noble metal catalyst on carbon at 20°–30° C. The catalyst is then removed by filtration and the solvent removed. The residue is IV which can be further purified by the usual techniques.

Once the ketone IV is obtained it can then be reacted with a suitable polyamine V. Polyamines V which are exceptionally suitable for reaction with ketone IV include N,N'-bis-(3-amino-2-hydroxypropyl)-1,4-cyclohexanebis(methylamine); N-(3-aminopropyl)-1,4-cyclohexanebis(methylamine); N,N'-bis-(3-aminopropyl)-1,4-bis-(2-aminoethyl)cyclohexane; N-(2-aminoethyl)-1,4-bis-(2-aminoethyl)cyclohexane; N(2-hydroxyethyl)-1,4-cyclohexanebis(methylamine); N,N-bis-(3-hydroxypropyl)-1,4-cyclohexanebis(methylamine); N-(2,3-dihydroxypropyl)-1,4-cyclohexanebis(methylamine); and N-(3-aminopropyl)-N'-(2-hydroxyethyl)-1,4-cyclohexanebis(methylamine).

Substituted bicycloheptanes which are obtained in the several syntheses routes described herein may be in exo and endo isomer configurations and generally are mixtures of both. Many factors enter into the actual ratio of isomers formed and these can be temperature, solvents, steric effects, equilibration conditions, nature of substituents and others. However, it appears that the utility of the products of this invention is served without the necessity for strictly controlling the isomer composition. The content of a product mixture may be determined by vapor or liquid phase chromatography, NMR spectral analysis, fractional distillation and other methods. It is also possible to isolate pure isomers by selection of these and other separation techniques well known in the art.

The following specific examples are further illustrative of our invention, but should not be construed as any limitation on the compound presented in formula I or the appended claims.

EXAMPLE A

Preparation of 5-Norbornen-2-Butyric Acid

To refluxing acetic anhydride (1050 g., 10 moles), there is added dropwise over six hours a solution of 5-vinyl-2-norbornene (120 g., 1 mole) and di-tert-butyl peroxide (0.1 mole, 14.6 g.). After complete addition, the mixture is heated at reflux for five hours. The cooled reaction mixture is concentrated under reduced pressure to leave a yellow-orange residual oil; 750 ml. of 2.5N NaOH is added to the residue which is then heated on the stream bath for one hour. The cooled solution is extracted once with ether, made acidic with concentrated HCl, and extracted thoroughly with ether. The dried ($Na_2SO_4$) ether extracts are concentrated under reduced pressure and the residue distilled under vacuum to give a colorless product, 35.5 g. (20%), b.p. 120°–124° C./0.2 mm.

Similarly, in an analogous manner, 3-(2-norbornen-5-yl)propionic acid is prepared from 5-ethylidene-2-norbornene; 1,5,5-trimethylnorborn-3-ylacetic acid from δ-fenchene; 5,5-dimethylnorborn-2- and 3-ylacetic acid from camphenilene; 2,5,5-trimethylnorborn-3-ylacetic acid from γ-fenchene; 3-(7,7-dimethylnorborn-2-yl)propionic acid from α-fenchene; 3-(3,3-dimethylnorborn-2-yl)propionic acid from camphene; 3-(norborn-2-yl)propionic acid from norcamphene; norborn-2-ylacetic acid from norbornylene; 7,7-dimethylnorborn-2-ylacetic acid from apobornylene; 1,7,7-trimethylnorborn-3-acetic acid from bornylene; 2,3-dimethylnorborn-2-ylacetic acid from santene; 3-(5,5-dimethylnorborn-2-en-6-yl)propionic acid from isocamphodiene; 3-(2,2-dimethylnorborn-5-yl)propionic acid from β-fenchene; 2,7,7-trimethylnorborn-3-ylacetic acid from ε-fenchene; 1,2,3-trimethylnorborn-3-ylacetic acid from ε-fenchene, and 1,2,3,4,5,5,6,6,7,7-decamethyl bicylco[2.2.1]heptane-3-yl-acetic acid from 1,2,3,4,5,5,6,6,7,7-decamethyl bicyclo[2.2.1]hept-2-ene obtained by the Diels Alder condensation of 1,1,2,3;4,5-hexamethylcyclopentadiene and 1,1,2,2-tetramethylethylene.

EXAMPLE B

Preparation Of Bicyclo[2.2.1]heptyl Substituted Alkanoic Acids

A solution of an alkyl alkanoate ester (15 mole), norbornene (14.1 g., 0.14 mole) and di-t-butyl peroxide (3.3 g., $2.25 \times 10^{-2}$ mole) is placed in a stainless steel 3-liter autoclave. The autoclave is purged with nitrogen and then rocked at 140° C. for 12 hours. After cooling, the contents of the autoclave are stripped free of unreacted norbornene, ester and peroxide decomposition products. The residual liquid, which constituted the reaction product is purified by fractional distillation.

Ethyl acetate and norbornene give ethyl norborn-2-ylacetate, b.p. 62° C./8.5 mm. in 64% yield and methyl isobutyrate and norbornene give methyl 2-methyl-2-(norborn-2-yl)propionate, b.p. 84° C./1.2 mm. in 55% yield. These esters are then hydrolyzed in aqueous hydrochloric acid giving (norborn-2-yl)acetic acid and 2-methyl-3-(norborn-2-yl)propionic acid.

EXAMPLE C

Preparation of 1,3-Di-(3,3-Dimethylnorborn-2-yl)-2-propanone 3,3-Dimethylnorborn-2-yl acetic acid (36.4 g., 0.20 mole) and iron (hydrogen reduced, 6.15 g., 0.11 mole) is heated for 1.5 hours at 195° C. under a nitrogen atmosphere. After that time, the temperature is increased to 290° C. and maintained at that temperature for three hours. The cooled reaction mass is extracted well with ether, filtered through Celite, and the ethereal extracts concentrated under vacuum. The residual reddish oil is distilled under vacuum to leave the product as a pale yellow liquid, 21.5 g., (71%), b.p. 156°–159° C./0.1 mm.

Similarly, in an analogous manner, 1,3-di-(norborn-2-yl)propanone is prepared from 2-norbornane acetic acid; 1,7-di-(5-norbornen-2-yl)-4-heptanone from 4-(5-norbornen-2-yl)butyric acid; 2,6-di-(5-norbornen-2-yl)-4-heptanone from 3-(5-norborn-2-yl)butyric acid; 1,3-bis-(1,5,5-trimethylnorborn-3-yl)propanone from 1,5,5-trimethylnorborn-3-ylacetic acid; 1,3-bis-(5,5-dimethylnorborn-2- and 3-yl)propanones from 5,5-dimethylnorborn-2- and 3-ylacetic acids; 1,3-bis-(2,5,5-trimethylnorborn-3-yl)propanone from 2,5,5-trimethylnorborn-3-ylacetic acid; 1,5-bis-(7,7-dimethylnorborn-2-yl)pentan-3-one from 3-(7,7-dimethylnorborn-2-yl)propionic acid; 1,5-bis-(3,3-dimethylnorborn-2-yl)pentan-3-one from 3-(3,3-dimethylnorborn-2-yl)propionic acid; 1,5-bis-(norborn-2-yl)pentan-3-one from 3-(norborn-2-yl)propionic acid; 1,3-bis- (norborn-2-yl)-propanone from norborn-2-ylacetic acid; 1,3-bis-(7,7-dimethylnorborn-2-yl)propanone from 7,7-dimethylnorborn-2-ylacetic acid; 1,3-bis-(1,7,7-trimethylnorborn-2-yl)-propanone from 1,7,7-trimethylnorborn-2-ylacetic acid; 1,3-bis-(2,3-dimethylnorborn-2-yl)propanone from 2,3-dimethylnorborn-2-ylacetic acid; 1,5-bis-(5,5-dimethylnorborn-2-en-6-yl)pentan-3-one from 3-(5,5-dimethylnorborn-2-en-6-yl)propionic acid; 1,5-bis-(2,2-dimethylnorborn-5-yl)pentan-3-one from 3-(2,2-dimethylnorborn-5-yl)propionic acid; 1,3-bis-(2,7,7-trimethylnorborn-3-yl)propanone from 2,7,7-trimethylnorborn-3-ylacetic acid; 1,3-bis-(1,2,3-trimethylnorborn-3-yl)propanone from 1,2,3-trimethylnorborn-3-ylacetic acid; 1,3-bis-[1,2,4,5,6,7-hexamethyl-7-propyl[2.2.1]hept-5-en-3-yl]acetone from 1,2,4,5,6,7-hexamethyl-7-propyl[2.2.1]-hept-5-en-3-ylacetic acid which is prepared by the Diels-Alder condensation of 1-methyl-1-propyl-2,3,4,5-tetramethylcyclopentadiene and 4-methylvinylacetic acid; bis-[1,2,2,3,4,5,6, 7,7-nonamethyl-bicyclo[2.2.1]hept-5-en-3-yl]acetone from 1,2,2,3,4,5,6,7,7-nonamethyl-bicyclo[2.2.1]hept-5-ene-3-ylacetic acid which is prepared by the Diels-Alder condensation of 1,1,2,3,4,5-hexamethylcyclopentadiene and 3,4,4-trimethyl vinyl acetic acid; 1,3-di-(2,4,6,6-tetramethyl-2-norpinen-3-yl)-2-propanone from 2,4,6,6-tetramethyl-2-norpinen-3-ylacetic acid; 1,3-di(2-pinen-4-yl)-2-propanone from 2-pinen-4-ylacetic acid; 1,5-bis- (6,6-dimethylnorpinan-4-yl)pentan-3-one from 3-(6,6-dimethylnorpinan-4-yl)propionic acid and 1,5-bis(norpinan-2yl)pentan-3one from 3-(norpinan-2-yl)propionic acid.

EXAMPLE D

Preparation of
2-(Bicyclo[2.2.1]heptan-2-ylacetyl)bicyclo[2.2.1]heptane

The sodio derivative of di-t-butyl bicyclo [2.2.1]heptan-2-ylmalonate is prepared by adding 0.36 g. of sodium hydride to a solution of the malonic ester, 3.1 g., in 75 ml. of anhydrous benzene. An Ascarite drying tube is attached to the reflux condenser. Reaction is effected by heating at 80° C. with stirring until hydrogen gas evolution ceases (approximately 2 ½ hours) A solution of 16 gms. of bicyclo[2.2.1.]heptan-2-ylcarboxylic acid chloride in 30 ml. of anhydrous benzene is then added and the reaction conducted at reflux for about 10 minutes. The mixture is cooled to room temperature and the excess sodium hydride destroyed by the addition of 0.9 g. of anhydrous p-toluene sulfonic acid. The mixture is clarified by filtration and the filtrate stripped of solvent under reduced pressure. The residue is dissolved in 75 ml. of glacial acetic acid containing 0.3 g. of anhydrous p-toluene sulfonic acid and 2% of acetic anhydride by volume. The solution is heated at reflux for 1 hour, cooled to room temperature, poured over crushed ice, neutralized by the addition of 5% sodium hydroxide solution and the product extracted with diethyl ether. The ether solution is washed with water dried over anhydrous magnesium sulfate, filtered and stripped of solvent. The residue is essentially pure 2-(bicyclo[2.2.1.]heptan-2-ylacetyl)-bicyclo[2.2.1]heptane.

Under the same reaction conditions, the following ketones are obtained:

1-[3-methylbicyclo[2.2.1]hept-2-yl]-6-[3,3-dimethylbicyclo[2.2.1]hept-2-yl]hexan-3-one from 3-methylbicyclo[2.2.1]hept-2-ylmethylmalonic ester and 4-[3,3-dimethylbicyclo[2.2.1]hept-2-yl]butyric acid chloride and 1-[5,6-diethylbicyclo[2.2.1]hept-2-yl]-4-[1,7,7-trimethylbicyclo[2.2.1]hept-2-yl]butan-2-one from 5,6-diethylbicyclo[2.2.1]hept-2-ylacetyl chloride and 1,7,7-trimethylbicyclo[2.2.1]hept-2-ylmethylmalonic ester.

EXAMPLE E

Preparation of 1
-(1,7,7-trimethylbicyclo[2.2.1]hept-2-yl)-4-(1,3,3-trimethylbicyclo[2.2.1]hept-2-yl)butan-2-one 20.6 gm. (0.1 mole) of 1-(1,3,3-trimethylbicyclo[2.2.1]hept-2-yl)-1-buten-3-one and 18.3 gm. (0.12 mole) of camphor is dissolved in 25 ml. methyl alcohol. A solution of 3.4 gm. of potassium hydroxide in 20 ml. of methyl alcohol is then added over a period of 15 minutes using good agitation and external cooling. The reaction mixture is maintained at 40°–45° C. for 6 hours, cooled to 20° C., made slightly acid by the addition of dilute hydrochloric acid and the residue after solvent stripping under reduced pressure extracted with ether. The ether solution is washed two times with one-tenth its volume of cold water, dried over anhydrous magnesium sulfate and stripped of solvent under reduced pressure. The residual oil which contained 1-(1,7,7-trimethylbicyclo[2.2.1]hept-2-ylidene)-4-(1,3,3-trimethylbicyclo[2.2.1]hept-2-yl)but-3-en-2-one is dissolved in 100 ml. of thiophene-free benzene and shaken under 50 psi hydrogen pressure in the presence of 3 gm. 5% palladium on carbon at 25° C. until slightly more than theoretical hydrogen uptake is observed. The catalyst is removed by filtration and the solvent stripped. The residual oil is purified by fractional distillation under reduced pressure to provide the 1-(1,7,7-trimethylbicyclo[2.2.1]hept-2-yl)-4-(1,3,3-trimethylbicyclo[2.2.1]hept-2-yl)butan-2-one.

In the same synthesis procedures the use of other aldehyde and ketone bicyclo[2.2.1]heptane derivatives provides a source of di-alicyclic alkanones:

| Aldehyde or Ketone | Ketone | Di-(bicycloheptyl)-alkanone |
|---|---|---|
| 3,3-dimethylbicyclo[2.2.1]-hept-2-ylaldehyde | 1-(1,3,3-trimethylbicyclo[2.2.1]-hept-2-yl)-1-buten-3-one | 1[3,3-dimethylbicyclo[2.2.1]hept-2-yl]-5-(1,3,3-trimethylbicyclo[2.2.1]hept-2-yl)pentan-3-one |
| 2,5-methylene-1,2,5,6-tetrahydrobenzaldehyde | 1-(1,3,3-trimethylbicyclo[2.2.1]-hept-2-yl)-1-buten-3-one | 1-[bicyclo[2.2.1]-hept-2-yl]-5-(1,3,3-trimethylbicyclo[2.2.1]hept-2-yl-pentan-3-one |
| 3-methyl-2-norbornanone | 1-(1,3,3-trimethylbicyclo[2.2.1]-hept-2-yl)-1-buten- | 1-[3-methylbicyclo[2.2.1]hept-2yl]-4-(1,3,3-trimethyl- |

| Aldehyde or Ketone | Ketone | Di-(bicycloheptyl)-alkanone |
|---|---|---|
| | 3-one | bicyclo[2.2.1]hept-2-yl)butan-2-one |
| 2-bornyl n-propyl ketone | 2-bornyl n-propyl ketone | 2-[2-ethyl-3-[1,7,7-trimethylbicyclo-[2.2.1]hept-2-yl]-hexanoyl]-1,7,7-trimethylbicyclo-[2.2.1]heptane |
| 3-[1,3,3-tri-methylbicyclo-[2.2.1]hept-2-yl]acrolein | 1-(1,3,3-trimethyl-bicyclo[2.2.1]hept-2-yl)-1-butene-3-one | 1,7-di-[1,3,3-tri-methylbicyclo[2.2.1]hept-2-yl]heptan-3-one |

EXAMPLE F

Preparation of 2-[1,7,7-trimethylbicyclo[2.2.1]hept-2-yl acetyl]bicyclo[2.2.1]heptane a. Preparation of the Grignard Reagent of (Bicyclo[2.2.1]hept-2-yl Bromide)

The reagent is prepared in dried apparatus under nitrogen by addition of 5.0 gm. (0.029 mole) of the bromide in 20 ml. of dry ether to 1.0 gm. (0.041 gm.-atom) of magnesium under 15 ml. of ether containing a crystal of iodine. The mixture is refluxed for 1 hour. This Grignard reagent can also be prepared according to the method of H. Kwart and L. Kaplan, J. Am. Chem. Soc., 76, 1072 (1954).

b. Reaction of Grignard Reagent with 1,7,7-Trimethyl-bicyclo[2.2.1]hept-2-yl-acetonitrile A solution of 3.5 gm. (0.02 mole) of 2-bornaneacetonitrile in 15 ml. of anhydrous ether is added over a 15 minute period of the well-stirred Grignard reagent from (a) above. After complete addition the reaction mixture is agitated for a total of 12 hours. It is then poured onto a mixture of 50 gm. ice and 20 ml. of concentrated hydrochloric acid. The ether is removed under reduced pressure and the residual mixture heated at reflux for 1 hour. The cooled mixture is extracted with 2–50 ml. portions of ether, the organic layer separated, washed with cold water, dried over anhydrous magnesium sulfate, filtered and the solvent removed by distillate. The residue is subjected to vacuum fractional distillation to obtain the 2-[1,7,7-trimethylbicyclo [2.2.1]hept-2-ylacetyl]bicyclo[2.2.1]heptane in pure state; typical IR carbonyl absorption at 5.8 microns is used to characterize the product.

Under the same conditions but substituting the following halides for norbornyl bromide and reaction of the corresponding Grignard reagent with 1,7,7-trimethylbicyclo[2.2.1]heptan-2-ylacetonitrile these intermediate ketones are obtained:

| Halide | Ketone |
|---|---|
| 2-[(2-bromoethyl)bicyclo-[2.2.1]heptane | 1-[1,7,7-trimethylbicyclo-[2.2.1]hept-2-yl]-4-[bicyclo[2.2.1]heptan-2-yl]butan-2-one |
| 2-(3-bromopropyl)bicyclo[2.2.1]heptane | 1-[1,7,7-trimethylbicyclo-[2.2.1]hept-2-yl]-5-[bicyclo[2.2.1]hept-2-yl]-pentan-2-one |
| 2-(3-bromopropyl)-5,6-diethyl)bicyclo[2.2.1]heptane | 1-[1,7,7-trimethylbicyclo-[2.2.1]hept-2-yl]-5-[(5,6-diethyl)bicyclo-[2.2.1]hept-2-yl]pentan-2-one |
| 2-chloromethyl-1,7,7-trimethylbicyclo[2.2.1]heptane | 1,3-bis[1,7,7-trimethylbicyclo[2.2.1]hept-2-yl-]-acetone |
| 7-bromobicyclo[2.2.1]heptane | 7-[1,7,7-trimethylbicyclo-[2.2.1]hept-2-ylacetyl]-bicyclo[2.2.1]heptane |

Additional examples which are prepared according to this procedure include:

| Halide | Nitrile | Ketone |
|---|---|---|
| 2-(2-bromoethyl)-bicyclo[2.2.1]-heptane | 1,7,7-trimethylbicyclo[2.2.1]hept-3-ylacetonitrile | 1-[1,7,7-trimethylbicyclo-[2.2.1]hept-3-yl]-4-[bicyclo[2.2.1]hept-2-yl]butan-2-one |
| 2-(4-bromobutyl)bicyclo[2.2.1]heptane | 1-methylbicyclo-[2.2.1]hept-3-ylacetonitrile | 1-(1-methylbicyclo[2.2.1]-hept-3-yl)-6-(bicyclo[2.2.1]-hept-2-yl]hexan-2-one |
| 2-(2-bromopropyl)bicyclo[2.2.1]heptane | 1,7,7-trimethylbicyclo[2.2.1]hept-3-ylacetonitrile | 1-(1,7,7-trimethylbicyclo-[2.2.1]hept-3-yl)-3-methyl-4-(bicyclo[2.2.1]hept-2-yl)butan-2-one |
| 2-(4-bromobutyl)-5-methylbicyclo[2.2.1]heptane | 3-(3-cyanopropyl)-1-methylbicyclo[2.2.1]heptane | 1-(1-methylbicyclo[2.2.1]-hept-3-yl)-8-(5-methylbicyclo[2.2.1]hept-2-yl)octan-4-one |

PREPARATION G

Preparation of N-(3-Aminopropyl)-1,4-cyclohexanebis(methylamine)

Acylonitrile (26.5 g., 0.5 mole) is added dropwise over a 45 minute period to 1,4-cyclohexanebis(methylamine) (2.84 g., 2.0 mole) with stirring and ice bath cooling. After complete addition, the reaction mixture is stirred an additional 1 hour at 5° C., gradually warmed to 45° C. and kept 2 hours at that temperature followed by 1 hour at 90° C. The reaction mixture is stripped of any unreacted acrylonitrile and excess non-cyanoethylated bis(methylamine) starting material which is removed at an internal temperature of 110° C. and 1 mm. The residue is then dissolved in 1.5 l. of ethyl alcohol (ammonia gas saturated) mixed with 50 ml. of sponge nickel catalyst and hydrogenated at 150 psi. After removal of catalyst by filtration, the solvent and ammonia are stripped off and the triamine product purified by fractionation under reduced pressure.

A higher homolog, N-(3-aminopropyl)-1,4-cyclohexanebis-(2-ethylamine) is synthesized using the above procedure with 1,4-bis-(2-aminoethyl)cyclohexane prepared according to P.P. Garcia and J.H. Wood, *J. Org. Chem.*, 26, 4167 (1961). Excess starting amine in this example may be separated from product at a boiling point of 122°–126° C./1 mm.

PREPARATION H

Preparation of N-(3-Aminopropyl)-N'-(2-hydroxyethyl)-1,4-cyclohexanebis(methylamine)

Acylonitrile (10.6 g., 0.2 mole) is added dropwise over a 15 minute period to N-(2-hydroxyethyl)-1,4-cyclohexanebis(methylamine (37.2 g., 0.4 mole) was stirring and ice bath cooling. After complete addition, the reaction mixture is stirred an additional 2 hours at 5° C., allowed to gradually warm over a 1 hour period, heated 2 hours at 45° C. and finally 1 hour at 90° C. It is then fractionated under reduced pressure up to an internal temperature of 170° C. The residue is dissolved in 200 ml. ethyl alcohol, cooled in an ice bath and saturated with ammonia gas at 0° C. Approximately 5 ml. of sponge nickel catalyst (W. R. Grace Co., Davison Chem. Division) is added and the mixture shaken under hydrogen at 150 psi until no further hydrogen uptake. The catalyst is removed by suction, filtration under nitrogen, the solvent stripped away and the residue fractionally distilled under reduced pressure. The triamine product is readily distinguished from cyanoethylated diamine by its lower $R_f$ on silica gel using a solution of 1 volume concentrated aqueous ammonium hydroxide in 4 volume alcohol. The synthesis is an adaptation of the method of M. Israel et al, *J. Med. Chem..*, 7, 710 (1964) for the preparation of polymethylenepolyamines.

PREPARATION I

Preparation of N-(2-Hydroxyethyl)-1,4-cyclohexanebis (methylamine)

A solution of 14.2 gm. (0.1 mole) of 1,4-cyclohexanebis(methylamine) in 150 ml. anhydrous methyl alcohol and under an atmosphere of nitrogen is warmed to 45°–50° C. In a 20 minute period, there is introduced with good agitation and beneath the liquid surface a total of 1.1 gm. (0.025 mole) of ethylene oxide in gaseous form. The reaction temperature is maintained at 45°–50° C. for an additional one-half hour after stopping the addition of ethylene oxide. The methyl alcohol is removed by distillation at atmospheric pressure; excess 1,4-cyclohexanebis(methylamine) is readily separated from the product by fractionation under reduced pressure. Only monoethoxylated compound remains and can be used as such or further purified by distillation at reduced pressure.

PREPARATION J

Preparation of N-(3-Amino-2-hydroxypropyl)-1,4-cyclohexanebis(methylamine)

1,4-cyclohexanebis(methylamine (14.2 g., 0.1 mole) is dissolved in 50 ml. of anhydrous methyl alcohol and the solution cooled to +5° C. in an ice bath. Epichlorohydrin (9.3 g., 0.1 mole) is added in a 2-minute period and the temperature maintained at +5° C. for 2 hours; reaction is allowed to continue at 10°–15° C. until thin layer chromatography of an aliquot (silica gel plate with development using a solution of 1 volume concentrated aqueous ammonium hydroxide in 4 volumes of methyl alcohol) indicates nearly complete conversion of the starting diamine to the propylene chlorohydrin. The solution is then added to 100 ml. of dry methyl alcohol previously saturated at 0° C. with dry ammonia gas by continuous dropwise flow at +5° C. with good agitation and external cooling. After stirring 2 hours at +5° C., it is allowed to warm to 20° C. and mixed overnight. The reaction is competed by heating at 45°–55° C. for 6 hours. The solvent and ammonia were removed by stripping and the product purified using fractional distillation under reduced pressure.

N-(2,3-Dihydroxypropyl)-1,4-cyclohexanebis-(methylamine) is produced by alkaline hydrolysis of the above propylenechlorohydrin derivative.

The propylene chlorohydrin derivative is dissolved in a 1M sodium hydroxide solution containing 50% methyl alcohol and 50% water by weight in a ratio of 5 grams of chlorohydrin to 25 ml. of sodium hydroxide solution. After stirring 24 hours at 20° C. the methyl alcohol is removed by distillation and the oil which separates is extracted with 100 ml. of diethyl ether. The extract is washed with approximately 10 ml. of cold water, the ether layer dried over anhydrous sodium sulphate and then filtered. Removal of the ether by distillation leaves the product in good purity as an oil.

PREPARATION K

Preparation of N,N'-bis-(3-Aminopropyl)-1,4-bis-(2-aminoethyl)cyclohexane

Acrylonitrile (10.6 g., 0.2 mole) is added dropwise over a 15 minute period to 1,4-bis- (2-aminoethyl)-cyclohexane (17.0 g., 0.1 mole) cooled in an ice bath and with good stirring. The resultant solution is maintained at 5°–10° C. with agitation for 1 hour, allowed to warm to 25° C. over a 2 hour period and finally heated at 90°–95° C. for 4 hours. The reaction mixture is then freed of any unreacted material and monocyanoethylated product by gradually heating to an internal temperature of 130° C. at a pressure of 0.5–1 mm. The residue is dissolved in 200 ml. ethyl alcohol which had been previously saturated with dry ammonia gas at 0° C., mixed with approximately 5 ml. of a sponge nickel catalyst suspension and reduced with shaking under 200 psi hydrogen. The catalyst is removed by suction filtration, the filtrate stripped of solvent and the residue purified by fractional distillation under reduced pressure.

PREPARATION L

Preparation of N-(2-Aminoethyl)-1,4-bis-(2-aminoethyl)- cyclohexane 1,4-Bis-(2-aminoethyl)cyclohexane (68 gm., 0.4 mole) and ethyleneimine (4.3 gm., 0.1 mole) with 0.4 g. ammonium chloride is mixed in a glasslined pressure reactor and filled with nitrogen to 100 psi. The mixture is shaken and heated to 85°–95° C. for 48 hours. After cooling, it is distilled rapidly free of the salt and then fractionated under high vacuum. The starting diamine is readily distinguished from the triamine product by thin layer chromatography and silica gel using a mixture of 1 volume concentrated aqueous ammonium hydroxide with 4 volume methyl alcohol, the diamine having a much higher $R_f$.

PREPARATION M

N,N-Bis-(3-hydroxypropyl)-1,4-cyclohexanebis(methylamine)

Preparation of 1-Cyano-4-[di-(3-hydroxypropyl)aminomethyl]- cyclohexane and catalytic reduction a. 1-Bromomethyl-4-cyanocyclohexane (20.2 g., 0.1 mole) and di-(3-hydroxypropyl)amine (53.2 g., 0.4 mole) in 400 ml. of anhydrous isopropyl alcohol is heated in an autoclave at 105° C.–115° C. for 8 hours with continuous agitation. The reaction mixture is stripped of solvent under reduced pressure and the residue diluted with 500 ml. of ice water. A cold solution of 5 g. of solium hydroxide in 100 ml. of water is added and the mixture extracted with two 150 ml. portions of methylene chloride. The organic phase is then washed with 50 ml. of ice water, dried overnight with anhydrous sodium sulfate, filtered and freed of solvent by distillation under reduced pressure.

b. The residual oil from a.) is taken up in 200 ml. of anhydrous ethyl alcohol previously saturated at 0° C. with dry ammonia gas, mixed with 5 ml. of sponge nickel catalyst suspension and hydrogenated at 25° C. under 100 psi hydrogen pressure in a stirred autoclave. The reaction completion is readily determined by disappearance of the C N IR absorption band and measurement of hydrogen uptake. The catalyst is removed by suction filtration, the solvent with mild heating under reduced pressure and the product obtained pure with fractional distillation at reduced pressure.

EXAMPLE 1

Preparation of 1-(2-Aminoethyl)-4- 2-[1,5-di-(3.3-dimethylnorborn-2-yl)-3-pentylamino]ethyl cyclohexane Dihydrochloride 1,5-Di-(3,3-dimethylnorborn-2-yl)-3-pentanone (6.04 g., 0.02 mole) and 1,4-bis-(2-aminoethyl)cyclohexane (10.1 g., 0.06 mole) in 150 ml. toluene is heated at reflux overnight with a Dean-Stark water separator. The cooled solution is concentrated under reduced pressure. The residue is dissolved in ethanol and hydrogenated with $PtO_2$ at room temperature and 40 psi hydrogen pressure. The platinum catalyst is filtered off and the ethanol removed under vacuum. The residual oil is dissolved in ether and the ether solution washed several times with water to remove the excess 1,4-bis-(2-aminoethyl)cyclohexane. The ether extracts are dried over anhydrous sodium sulfate and concentrated under vacuum to leave the polyamine product.

The oil is dissolved in ether and hydrogen chloride gas is bubbled into the solution until no further precipitation occurs. The ether is evaporated under reduced pressure to leave the product as a solid which is digested with hot isopropyl alcohol. The solids are collected by filtration and dried under vacuum at 70° C. to give a nearly colorless product.

In an analogous manner regarding quantities and reaction conditions and using 1,5-di-(3,3-dimethylnorborn-2-yl)-3-pentanone and the amines set forth below, there are prepared the following compounds of this invention.

| Amine | Product |
| --- | --- |
| N,N'-bis-(3-aminopropyl)-1,4-bis-(2-aminoethyl)cyclohexane | N-(3-aminopropyl)-N'-{3-[1,5-di-(3,3-dimethylnorborn-2-yl)-3-pentylamino]propyl}-1,4-bis(2-aminoethyl)cyclohexane |
| N-(3-aminopropyl)-N'-2-hydroxyethyl-1,4-cyclohexanebis-(methylamine) | N-{3-[1,5-di-(3,3-dimethylnorborn-2-yl)-3-pentylamino]propyl}-N'-(2-hydroxyethyl)-1,4-cyclohexanebis(methylamine) |
| N-(2,3-dihydroxypropyl)-1,4-cyclohexanebis(methylamine) | N-(2,3-dihydroxypropyl)-N'-[1,5-di-(3,3-dimethylnorborn-2-yl)-3-pentyl]-1,4-cyclohexanebis(methylamine) |
| N,N'-bis-(3-amino-2-hydroxypropyl)-1,4-cyclohexanebis-(methylamine) | N-(3-amino-2-hydroxypropyl)-N'-{3-[1,5-di-(3,3-dimethylnorborn-2-yl)-3-pentylamino]-2-hydroxypropyl}-1,4-cyclohexanebis(methylamine) |
| N-(3-aminopropyl)-1,4-cyclohexanebis(methylamine) | Mixture of N-(3-aminopropyl)-N'-[1,5-di-(3,3-dimethylnorborn-2-yl)-3-pentyl]-1,4-cyclohexanebis(methylamine) and N-{3-[1,5-di-(3,3-dimethylnorborn-2-yl)-3-pentylamino]propyl}-1,4-cyclohexanebis-(methylamine) |
| N,N'-bis-(3-aminopropyl)-1,4-cyclohexanebis(methylamine) | N-(3-aminopropyl)-N'-{3- [1,5-di-(3,3-dimethylnorborn-2-yl)-3-pentylamino]propyl}-1,4-cyclohexanebis(methylamine) |

Further, in an analogous manner regarding quantities and reaction conditions by employing 1,3-di-(3,3-dimethylnorborn-2-yl)-2-propanone and respectively N,N'-bis-(3-aminopropyl)-1,4-bis-(2-aminoethyl)cyclohexane and N-(3-aminopropyl)-N'-2-hydroxyethyl-1,4-cyclohexanebis(methylamine) there are prepared the hydrochlorides of N-(3-aminopropyl)-N'-{[1,3-di-(3,3-dimethylnorborn-2-yl)-2-propylamino]propyl}-1,4-bis(2-aminoethyl)cyclohexane and N-{3-[1,3-di-(3,3-dimethylnorborn-2-yl)-2-propylamino]propyl}-N'-(2-hydroxyethyl)-1,4-cyclohexanebis(methylamine), respectively.

EXAMPLE 2

Preparation of N-(2-Hydroxyethyl)-N'-[1,5-di-(2-norbornyl)-3-pentyl]-1,4-cyclohexanebis(2-ethylamine) Dihydrochloride 1,5-Di-(2-norbornyl)-3-pentanone (4.15 g., 0.015 mole) and N-(2-hydroxyethyl)cyclohexane-1,4-bis-(2-ethyl- amine) (21.4 g., 0.1 mole) in 150 ml. of toluene is heated at reflux for three hours. The cooled solution is hydrogenated with PtO$_2$ at room temperature and 40 psi hydrogen pressure. The platinum catalyst is filtered off and the ethanol removed under vacuum. The residual oil is dissolved in ether and the ether solution is washed several times with water. The dried (anhydrous sodium sulfate) ether extracts are concentrated under vacuum to leave the olyamine as an oil.

The oil is dissolved in absolute methanol and cooled in an ice-water bath. Hydrogen chloride gas is bubbled into the solution. The methanol is evaporated under reduced pressure to leave a gummy solid which is recrystallized from isopropyl alcohol to leave the product as colorless crystals.

Also prepared by this method are N-[1,3-di-(2-norbornyl)-2-propyl]-1,4-bis-(2-aminoethyl)cyclohexane dihydrochloride from 1,3-di-(2-norbornyl)-2-propanone and 1,4-bis-(2-aminoethyl)cyclohexane; N-(3-aminopropyl)-N'-{3-[1,3-di-(2-norbornyl)-2-propylamino]propyl}-1,4-bis-(2aminoethyl)cyclohexane tetrahydrochloride from 1,3-di-(2-norbornyl)-2-propanone and N,N'-bis-(3-amino-propyl)-1,4-bis-(2-aminoethyl)cyclohexane; N-[1,7-di(2-norbornyl)-4-heptyl]-1,4-bis-(2-aminoethyl)cyclohexane dihydrochloride from 1,7-di-(2-norbornyl-4-heptanone and 1,4-bis-(2-aminoethyl)cyclohexane; N-[2,6-di(2-norbornyl)- 4-heptyl]-1,4-bis-(2-aminoethyl)cyclohexane dihydrochloride from 2,6-di-(2-norbornyl)-4-heptanone and 1,4-bis-(2-aminoethyl) cyclohexane.

EXAMPLE 3

Preparation of
N-[1,7-Di-(5-norbornen-2-yl)-4-heptyl]-1,4-bis-(2-aminoethyl) cyclohexane Dihydrochloride 1,7-Di(5-norbornen-2-yl)-4-heptanone (5.96 g., 0.02 mole) and 1,4-bis-(2-aminoethyl)cyclohexane (17.2 g., 0.10 mole) in 150 ml. of toluene is heated at reflux overnight with a Dean-Stark water separator. The toluene is then removed under vacuum. The residual oil dissolved in 25 ml. isopropanol is added dropwise to sodium borohydride (1.90 g., 0.05 mole, excess) suspended in 50 ml. isopropanol. After complete addition, the reaction mixture is heated at reflux for one hour. The isopropanol is evaporated under reduced pressure, the residue treated with water and the aqueous mixture extracted well with ether. The combined ether extracts are back-washed with water, a saturated sodium chloride solution, dried over anhydrous sodium sulfate and concentrated under vacuum to have the amine product as an oil.

The oil is dissolved in ether and the solution cooled in an ice-water bath. Hydrogen chloride gas is bubbled into the solution until no further precipitate is formed. The solid is collected by filtration, washed with a small amount of ether, and dried under vacuum to leave the amine dihydrochloride as a nearly colorless product.

EXAMPLE 4

Preparation of
N-(3Aminopropyl)-N'-[1,5-di-(3,3-dimethylnorborn-2-yl)-3-pentyl]-1,4-cyclohexanebis(methylamine)

A mixture of 1,5-de-(3,3-dimethylnorborn-2-yl)-3-pentanone (9.9 g., 0.03 mole) and 1,4-cyclohexanebis(methylamine) (28.4 g., 0.20 mole) in 250 ml. ethanol is heated at reflux overnight. The cooled reaction mixture is hydrogenated with PtO$_2$ at room temperature and 40 psi hydrogen pressure. The platinum catalyst is filtered off and the ethanol removed under reduced pressure. The residual oil is dissolved in ether and the ether solution washed several times with water to remove the unreacted diamine. The ether extracts are dried over anhydrous sodium sulfate and concentrated under vacuum to leave a colorless oil.

The oil is dissolved in 20 ml. tert-butanol and chilled to 0°-5° C. in an ice-water bath. Acrylonitrile (1.75 g., 2.2 ml., 0.033 mole) is added dropwise over a 5-minute period. The reaction mixture is allowed to warm up to room temperature and is then heated at 60° C. overnight. The t-butanol was removed under reduced pressure. The residual oil was dissolved in 150 ml. glacial acetic acid and hydrogenated with PtO$_2$ at room temperature and 40 psi hydrogen pressure. The platinum catalyst is filtered off and the acetic acid removed under vacuum. The residue is dissolved in ether and made basic with 10% sodium hydroxide. The ether solution is washed with water, dried over anhydrous sodium sulfate and concentrated under reduced pressure to leave the product as an oil. It can be brought to analytical purity by chromatography on activity III Woelm alumina with chloroform and chloroform-methanol mixtures.

In addition, the compounds of this invention set forth in the table below are prepared by the reactions set forth in the previous examples. It should be noted, however, that [3.1.1) bicycloheptenes tend to undergo rearrangement when attempts are undertaken to introduce substituents by free radical mechanisms as in Example A. Therefore, it is preferred that [3.1.1]bicyclic heptyl carboxylic acids be obtained by other means well known in the art.

TABLE I

| A$_1$ | Ketone R$_1$,R$_2$ | n | Amine | Schiff Base Red. Via | Product |
|---|---|---|---|---|---|
| 2,4,6,6-tetramethyl-2-norpinen-3-yl | Ethylene " | 1 | N,N'-bis-(3-aminopropyl)-1,4-cyclohexanebis-(methylamine) | PtO$_2$ | N-(3-aminopropyl)-N'-{3-[1,5-di-(2,4,6,6-tetra-methylnorpinan-3-yl)-3-pentylamine]propyl}-1,4-cyclohexanebis(methylamine) |
| 2,4,6,6-tetramethyl-2-norpinen-3-yl | Ethylene " | 1 | 1,4-cyclohexanebis-(ethylamine | NaBH$_4$ | N-[1,5-di-(2,4,6,6-tetra-methyl-2-norpinen-3-yl)-3-pentyl]-1,4-cyclohexanebis-(ethylamine) |
| 2,4,6,6-tetramethyl-2-norpinen-3-yl | Ethylene " | 1 | N-(2,3-dihydroxypropyl)-1,4-cyclohxanebis-(methylamine) | PtO$_2$ | N-(2,3-dihydroxypropyl)-N'-[1,5-di-(2,4,6,6-tetramethyl-norpinan-3-yl)-3-pentyl]-1,4-cyclohexanebis(methylamine) |
| 3-pinanyl | Methylene Ethylene | 1 | N,N'-bis-(3-amino-2-hydroxypropyl)-1-4-cyclo-hexanebis(methylamine) | PtO$_2$ | N-(3-amino-2-hydroxypropyl)-N'-{3-[1,4-di-(3-pinanyl)-2-butylamino]-2-hydroxypropyl}-1,4-cyclohexanebis(methylamine) |
| 4-pinanyl | Trimethyl- | 1 | N-(2-hydroxyethyl)-1,4- | PtO$_2$ | N-(2-hydroxyethyl)-N'-[1,7- |

TABLE I-continued

| A₁ Ketone | R₁,R₂ | n | Amine | Schiff Base Red. Via | Product |
|---|---|---|---|---|---|
| | ene | | cyclohexanebis(ethylamine) | | di-(4-pinanyl)-4-heptyl]-1,4-cyclohxanebis(ethylamine) |
| 2-pinen-4-yl) | 2-methyl-trimethyl-ene ″ | 1 | N,N-bis-(3-hydroxypropyl)-1,4-cyclohxanebis(methyl-amine) | NaBH₄ cyclohex-anebis(me-thylamine) | N-[2,6-dimethyl-1,7-di-(2-pinen-3-yl)-4-heptyl]-N',N'-bis-(3-hydroxypropyl)-1,4- |
| 2-pinen-4-yl | Methylene 2-methyl-trimethyl-ene | 1 | 1,4-cyclohexanebis(ethyl-amine) | NaBH₄ | N-[4-methyl-1,5-di-(2-pinen-4-yl)-2-pentyl]-1,4-cyclohexane-bis(ethylamine) |
| 3-pinen-3-yl | Ethylene Methylene | 1 | N-(3-aminopropyl-N'-(2-hydroxyethyl)-1,4-cyclo-hexanebis(methylamine) | NaBH₄ | N-(2-hydroxyethyl)-N'-{3-[1,4-di-(3-pinen-3-yl)-2-butylamino]-propyl}-1,4-cyclohexanebis-(methylamine) |
| 3-pinen-3-yl | Methylene Methylene | 1 | N-(3-aminopropyl)-N'-(2-hydroxyethyl)-1,4-cyclo-hxanebis(methylamine) | NaBH₄ | N-(2-hydroxyethyl)-N'-{3-[1,3-di-3-pinen-3-yl)-2-propylamino]-propyl}-1,4-cyclohexanebis-(methylamine) |
| 2-norpinanyl | Ethylene | 1 | N,N'-bis-(2-aminoethyl)-1,4-cyclohexanebis(methyl-amine) | PtO₂ | N-(2-aminoethyl)-N'-{2-[1,5-di-(2-norpinanyl)-3-pentylamino]-ethyl}-1,4-cyclohexanebis-(methylamine) |
| 3-norpinanyl | Methylene | 1 | N,N'-bis-(3-aminopropyl)-1,4-cyclohexanebis(methyl-amine) | PtO₂ | N-(3-aminopropyl)-N'-{-[1,3-di-(3-norpinanyl)-2-propylamino]propyl}1,4-cyclohexanebis(methylamine) |
| 3-norpinanyl | Ethylene | 1 | N,N-di-(2-hydroxyethyl)-1,4-cyclohexanebis(ethyl-amine) | PtO₂ | N,N-di-(2-hydroxyethyl)-N'-{2-[1,5-di-(3-norpinanyl)-3-pentylamino]ethyl}-1,4-cyclo-hexanebis(ethylamine) |

Also each of the respective ketones IV set forth in Examples C, D, E and F when reacted with each of the individual amines set forth in this specification, firstly, according to the method set forth in Example 1, and then secondly according to Example 3 produces the entire range of compounds described according to this invention as embodied in Formula I.

The polyamines described herein are excellent broad spectrum antimicrobial agents which are especially effective against gram positive and negative bacteria, particularly the troublesome gram-negative of the genus Pseudomonas at aqueous concentrations of at least 1.0 to 100 ppm and higher. Examples of susceptible species include, inter alia, *Staphylococcus aureus, Streptococcus pyogenes, Bordetella bronchiseptica, Pasteurella multocida, Escherichia coli, Salmonella typhimurium, S. pullorum, Klebsiella pneumoniae, Aerobacter aerogenes, Pseudomonas aeruginosa, Desulfovibrio desulfuricans, Bacillus mycoides*, fungi such as *Aspergillus niger* and *Chaetomium globosum*. For use, these compounds can be applied neat or employed in a diluted form. Satisfactory diluents include any inert material not destructive of the antimicrobial activity and especially liquid formulations comprising aqueous dispersions, solutions, and emulsions. Solid diluents include talc, corn starch, alumina and diatomaceous earth. The antimicrobial agents of this invention can also be deposed on materials such as natural fibers including paper, cotton, wool and synthetic fibers such as nylon, polypropylene, as well as upon inanimate surfaces including hard surfaces such as wood, glass, metal, tile, rubber, plastic, and porous surfaces such as concrete, leather and the like.

The polyamines of this invention are especially useful in suppressing the growth of aerobic and anaerobic bacteria in fluids employed in cutting and grinding operations, such as metal working, and oil well drilling muds or secondary oil recovery waters and brines. Anaerobes such as the sulfate-reducer, *Desulfovibrio desulfuricans*, are inhibited at 0.1–10 ppm. concentration of these polyamines. Suppression of these bacteria eliminates hydrogen sulfide production and corrosion of equipment, plugging of oil-bearing sands, malodors and other deleterious actions. These compounds are also useful in the preservation against biodeterioration of other aqueous systems such as aqueous emulsions and dispersions, paints or coatings, pigment suspensions, adhesives and the like where proliferation of microorganisms can produce colloid breakdown, pH shifts, malodors, corrosive substances, viscosity loss and other undesirable effects.

One particularly useful application of the compounds of this invention is imparting sanitizing properties to fabrics, either woven or non-woven, launderable or disposable which are to be employed, such for example, as diapers, surgical masks, caps, gowns, towels and drapes, covers for hospital furniture and instrument wrappings, aseptic facial tissues and sanitary napkins and bathroom tissue. In this application, the compounds of Formula I can be applied to the fibrous pulp before extracting or strand or thread formation or it can be sprayed upon the finished goods. Either deposition technique is satisfactory so long as from $1 \times 10^{-4}\%$ or more by weight of the antimicrobial material is retained on the cloth. Greater than 0.1% to 1% by weight is generally excessive and superfluous.

Another application is alone or in solution or suspension or in conjunction with soaps or detergents for use in cleansing the skin, particularly in presurgical scrubbing formulations, or in formulations for controlling the growth of *Corynebacterium acnes*. *C acnes* is a strain of bacteria implicated in acne conditions, especially *Acne vulgaris*, wherein applications of as little as 1 to 5 ppm. is effective in controlling such skin dwelling bacteria. Larger concentrations can be used if desired without irritation or discomfort such as 2500 ppm and higher. Where the cleansing formulation is diluted with water upon use, the formulation can comprise from 0.01% by weight and more of the polyamine of this invention.

In addition, the compounds described herein can be employed in impounded water, such as swimming pools, ponds or industrially-used water such as a papermill water to inhibit growth of undesirable bacteria, fungi, and/or algae at levels as low as 0.5–5 ppm.

In the control of slime-producing microorganisms and algae in recirculating industrial waters, particularly cooling operations and especially installations such as cooling towers, the polyamine compounds of this invention are usually employed alone, but can also be used in combination with other antimicrobial agents. The compounds are preferably employed as salts to enhance solubility. Concentrations in the recirculating water of as little as $1 \times 10^{-4}\%$ by weight are effective in inhibiting microbial growth. To insure effectiveness, especially against more resistant strains of microorganisms, and also when make-up water is added to replace water lost by evaporation and the like, concentrations of from $1 \times 10^{-4}\%$ to $5 \times 10^{-2}\%$ by weight are most satisfactory. Dosage may be continuous or as intermittent "shock treatment", i.e., addition in a 10–20 minute period every 4–8 hours or even longer time spans.

An unusual, highly advantageous property of these compounds is high substantivity to all kinds of surfaces; this provides protection against corrosion and acts as a storage depot for continuously dosing the waters in contact. The same properties also are largely responsible for the previously stated utility as disinfectants for inanimate surfaces comprising walls and ceilings, equipment, animal pens, hospital facilities, kitchens and bathrooms and the like.

In formulating the compounds of this invention for the above uses, these compounds can be employed in combination with other antimicrobial agents, surfactants, insecticides, defoamers, odorants, or as chelates of metals such as copper, calcium, magnesium and iron.

What is claimed is:

1. A compound of the formula:

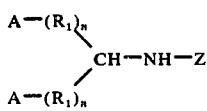

where:
each A is alike or different and is a bicyclic group of the formula:
a.

a)

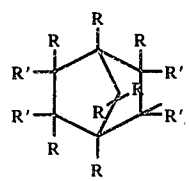

or a bicyclic group of the formula:
b.

b)

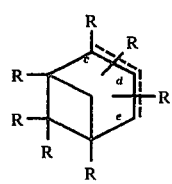

where R is alike or different and is hydrogen or $C_1$ to $C_4$ alkyl, R' is alike or different and is hydrogen or $C_1$ to $C_4$ alkyl or R' on adjacent carbon atoms taken together comprise an olefinic bond, and the dashed line indicates either saturation or c-, d-, e- unsaturation;

each $R_1$ is alike or different and is $C_1$ to $C_4$ alkylene:
each $n$ is alike or different and is the integer 0 to 1;
Z is

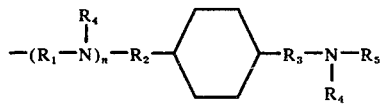

where
$R_2$ is 2-hydroxy-1,3-trimethylene, or $R_1$ as previously defined;
$R_3$ is 2-hydroxy-1,3-trimethylene, or $R_1$ as previously defined;
$R_4$ is hydrogen, aminoethyl, aminopropyl, $C_1$ to $C_4$ hydroxyalkyl, aminohydroxy $C_2$ to $C_4$ alkyl, or $C_2$ to $C_4$ dihydroxyalkyl;
$R_5$ is hydrogen, $C_1$ to $C_4$ hydroxyalkyl or $C_2$ to $C_4$ dihydroxyalkyl, aminohydroxy $C_2$ to $C_4$ alkyl, and $n$ is as previously defined, and acid addition salts thereof.

2. A compound according to claim 1 where R' and R are hydrogen or methyl.

3. A compound according to claim 1 where each A is a bicyclic group.

4. A compound according to claim 3 where $n$ is 1.

5. A compound according to claim 1 where Z is 1,4-bis-(2-aminoethyl)cyclohexane.

6. A compound according to claim 1 where Z is 1,4-cyclohexanebis(methylamine).

7. A compound according to claim 1 where Z is N-(3-aminopropyl)-N'-1,4-bis-(2-aminoethyl)cyclohexane.

8. A compound according to claim 1 where Z is N-(2,3-dihydroxypropyl)-N'-1,4-cyclohexanebis(methylamine).

9. A compound according to claim 1 where Z is N-(3-aminopropyl)-N'-1,4-cyclohexanebis(methylamine).

10. A compound of the formula:

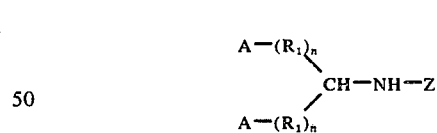

where:
each A is alike or different and is a bicyclic group of the formula:

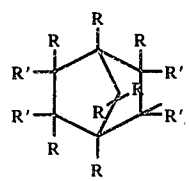

where R is alike or different and is hydrogen or $C_1$ to $C_4$ alkyl, R' is alike or different and is hydrogen or $C_1$ to $C_4$ alkyl or R' on adjacent carbon atoms taken together comprise an olefinic bond;

each $R_1$ is alike or different and is $C_1$ to $C_4$ alkylene:
each $n$ is alike or different and is the integer 0 to 1;
Z is

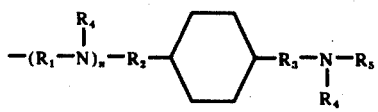

where
$R_2$ is 2-hydroxy-1,3-trimethylene, or $R_1$ as previously defined;
$R_3$ is 2-hydroxy-1,3-trimethylene, or $R_1$ as previously defined;
$R_4$ is hydrogen, aminoethyl, aminopropyl, $C_1$ to $C_4$ hydroxyalkyl, aminohydroxy $C_2$ to $C_4$ alkyl, or $C_2$ to $C_4$ dihydroxyalkyl;
$R_5$ is hydrogen, $C_1$ to $C_4$ hydroxyalkyl or $C_2$ to $C_4$ dihydroxyalkyl, aminohydroxy $C_2$ to $C_4$ alkyl, and $n$ is as previously defined, and acid addition salts thereof.

11. A compound according to claim 10 where R and R' are hydrogen or methyl, and less than five of the R and R' groups are methyl.

12. A compound according to claim 10 where A is a bicycloheptenyl and two R' on adjacent carbon atoms comprise an olefinic bond, the other R' and R are alike or different and are hydrogen or methyl.

13. A compound according to claim 11 where $n$ in $(R_1)_n$ is 1.

14. A compound according to claim 12 where $n$ in $(R_1)_n$ is 1.

15. A compound according to claim 10 where A is 3,3-dimethylnorborn-2-yl.

16. A compound according to claim 10 where A is norborn-2-yl.

17. A compound according to claim 15 where $R_1$ is ethylene.

18. A compound according to claim 16 where $R_1$ is ethylene.

19. A compound according to claim 15 where $R_1$ is methylene.

20. A compound according to claim 16 where $R_1$ is methylene.

21. A method of preparing compounds of the formula:

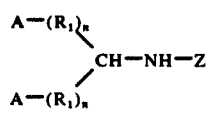

comprising reacting a compound of the formula:

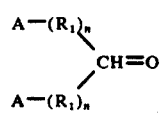

with a compound of the formula:

$H_2N-Z$, and then reducing the resulting Schiff base where:
each A is alike or different and is a bicyclic group of the formula:

a) 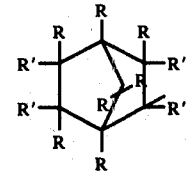

or a bicyclic group of the formula:

b) 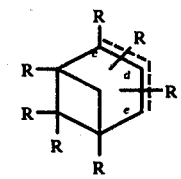

where R is alike or different and is hydrogen or $C_1$ to $C_4$ alkyl, R' is alike or different and is hydrogen or $C_1$ to $C_4$ alkyl or R' on adjacent carbon atoms taken together comprise an olefinic bond, and the dashed line indicates either saturation or c-, d-, e-, unsaturation;
each $R_1$ is alike or different and is $C_1$ to $C_4$ alkylene;
each $n$ is alike or different and is the integer 0 to 1;
Z is

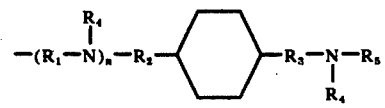

where
$R_2$ is 2-hydroxy-1,3-trimethylene, or $R_1$ as previously defined;
$R_3$ is 2-hydroxy-1,3-trimethylene, or $R_1$ as previously defined;
$R_4$ is hydrogen, aminoethyl, aminopropyl, $C_1$ to $C_4$ hydroxyalkyl, aminohydroxy $C_2$ to $C_4$ alkyl, or $C_2$ to $C_4$ dihydroxyalkyl;
$R_5$ is hydrogen, $C_1$ to $C_4$ hydroxyalkyl or $C_2$ to $C_4$ dihydroxyalkyl, aminohydroxy $C_2$ to $C_4$ alkyl, and $n$ is as previously defined, and acid addition salts thereof.

22. A composition comprising an antimicrobially effective amount of a compound of the formula:

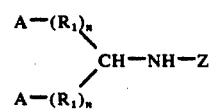

where:
each A is alike or different and is a bicyclic group of the formula:

a) 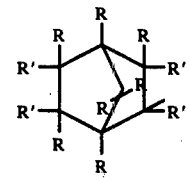

or a bicyclic group of the formula:

b) 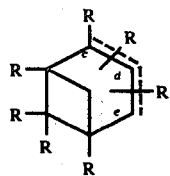

where R is alike or different and is hydrogen or $C_1$ to $C_4$ alkyl, R' is alike or different and is hydrogen or $C_1$ to $C_4$ alkyl or R' on adjacent carbon atoms taken together comprise an olefinic bond, and the dashed line indicates either saturation or c-, d-, e- unsaturation;

each $R_1$ is alike or different and is $C_1$ to $C_4$ alkylene;
each $n$ is alike or different and is the integer 0 to 1;
Z is

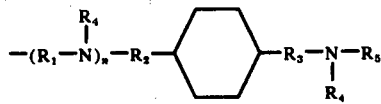

where
$R_2$ is 2-hydroxy-1,3-trimethylene, or $R_1$ as previously defined;
$R_3$ is 2-hydroxy-1,3-trimethylene, or $R_1$ as previously defined;
$R_4$ is hydrogen, aminoethyl, aminopropyl, $C_1$ to $C_4$ hydroxyalkyl, aminohydroxy $C_2$ to $C_4$ alkyl, or $C_2$ to $C_4$ dihydroxyalkyl;
$R_5$ is hydrogen, $C_1$ to $C_4$ hydroxyalkyl or $C_2$ to $C_4$ dihydroxyalkyl, aminohydroxy $C_2$ to $C_4$ alkyl, and $n$ is as previously defined, and acid addition salts thereof, and a carrier.

* * * * *